United States Patent
Engwall et al.

(10) Patent No.: US 11,602,644 B2
(45) Date of Patent: Mar. 14, 2023

(54) DETERMINING A DISTRIBUTION OF SPOTS OF VARYING SIZES FOR ION BEAM THERAPY BASED ON USER CONFIGURATION

(71) Applicant: RaySearch Laboratories AB, Stockholm (SE)

(72) Inventors: Erik Engwall, Hägersten (SE); Lars Glimelius, Stockholm (SE); Martin Janson, Enskededalen (SE)

(73) Assignee: RaySearch Laboratories AB, Stockholm (SE)

( * ) Notice: Subject to any disclaimer, the term of this patent is extended or adjusted under 35 U.S.C. 154(b) by 106 days.

(21) Appl. No.: 16/625,895

(22) PCT Filed: Jun. 26, 2018

(86) PCT No.: PCT/EP2018/067127
§ 371 (c)(1),
(2) Date: Dec. 23, 2019

(87) PCT Pub. No.: WO2019/002302
PCT Pub. Date: Jan. 3, 2019

(65) Prior Publication Data
US 2020/0147410 A1    May 14, 2020

(30) Foreign Application Priority Data
Jun. 30, 2017 (EP) .................................. 17179031

(51) Int. Cl.
*A61N 5/10* (2006.01)
(52) U.S. Cl.
CPC ......... *A61N 5/1031* (2013.01); *A61N 5/1077* (2013.01); *A61N 2005/1087* (2013.01)

(58) Field of Classification Search
CPC .... A61N 5/1031; A61N 5/103; A61N 5/1077; A61N 2005/1087
See application file for complete search history.

(56) References Cited

U.S. PATENT DOCUMENTS

| 2004/0104354 A1 | 6/2004 | Haberer et al. |
| 2009/0189095 A1* | 7/2009 | Flynn ....................... A61N 5/10 250/492.3 |

(Continued)

FOREIGN PATENT DOCUMENTS

| JP | 2001-212253 A | 8/2001 |
| JP | 2010-029594 A | 2/2010 |

(Continued)

OTHER PUBLICATIONS

First Examination Report dated Feb. 23, 2022 in Indian Patent Application No. 201917039250 (w.English translations).

(Continued)

*Primary Examiner* — Carrie R Dorna
(74) *Attorney, Agent, or Firm* — Faegre Drinker Biddle & Reath LLP

(57) ABSTRACT

It is provided a method for determining a distribution of spots for use with ion beam therapy for providing the spots in a target volume, wherein each spot represents a collection of ions of a specific energy level and of a specific size at a specific lateral location. The method is performed in a treatment planning system and comprises the steps of: dividing the target volume in a plurality of target sections based on a user configuration comprising at least one spot size strategy defining a maximum spot size at the location of a Bragg peak; assigning a spot size strategy to each one of the target sections based on the location of the respective target section; and determining, within each target section, spots in accordance with its spot size strategy.

13 Claims, 4 Drawing Sheets

(56) References Cited

U.S. PATENT DOCUMENTS

| | | | |
|---|---|---|---|
| 2011/0108737 A1 | 5/2011 | Pu et al. | |
| 2012/0056098 A1 | 3/2012 | Harada | |
| 2014/0350322 A1 | 11/2014 | Schulte et al. | |
| 2015/0090894 A1 | 4/2015 | Zwart et al. | |
| 2016/0220843 A1* | 8/2016 | Iwata | A61N 5/1077 |
| 2017/0281980 A1* | 10/2017 | Wulff | H01J 37/08 |
| 2020/0129781 A1* | 4/2020 | Engwall | A61N 5/1043 |

FOREIGN PATENT DOCUMENTS

| | | | |
|---|---|---|---|
| JP | 2016-532462 A | 10/2016 | |
| WO | WO-2018009779 A1 * | 1/2018 | A61N 5/1045 |

OTHER PUBLICATIONS

Search Report dated Feb. 25, 2022 in Japanese Patent Application No. 2019-571053 (16 pages) with an English translation (19 pages).

* cited by examiner

DETERMINING A DISTRIBUTION OF SPOTS OF VARYING SIZES FOR ION BEAM THERAPY BASED ON USER CONFIGURATION

This application is the national stage application under 35 U.S.C. § 371 of International Application No. PCT/EP2018/067127, filed on Jun. 26, 2018, and claims benefit of European Patent Application No. 17179031.4, filed on Jun. 30, 2017, both of which are incorporated herein by reference in their entirety.

TECHNICAL FIELD

The invention relates to a method, a treatment planning system, a computer program and a computer program product for distribution of spots of varying sizes for use with ion beam therapy for providing the spots in a target volume. The distribution and size of the spots are determined based on a user configuration.

BACKGROUND

In ion beam therapy, a beam of ions (e.g. protons or ions) is directed towards a target volume. The target volume can e.g. represent a cancer tumour. The particles penetrate the tissue and deliver a dose of energy to induce cell death. An advantage of ion beam therapy is that there is a significant peak in the dose distribution, known as a Bragg peak. The Bragg peak is a peak of dose delivery occurring at a certain depth, after which the dose delivery falls off quickly. This can be compared with electron beam therapy or X-ray therapy where the maximum dose always occurs at shallow depth and distal dose fall off cannot be controlled with the same sharp fall-off as for ion therapy.

The depth of the Bragg peak in the patient can be controlled by adjusting the kinetic energy of the particles. Lateral position can be controlled using electromagnets to deflect the focused beam. This allows for delivery of highly localized doses at well-controlled positions in the patient. The dose delivered from a certain combination of kinetic energy, and lateral deflection of the beam is referred to as a spot. The number of particles delivered to a spot is commonly referred to as the spot weight. By providing spots in many different locations in a three-dimensional space, the target volume can be covered with the desired dose distribution. The kinetic energies of the spots are often, but not necessarily, distributed over a number of discrete energies. A group of spots with the same kinetic energy, but different lateral deflection is often referred to as an energy layer. This procedure is called active scanning ion beam therapy, also known as pencil beam scanning.

The planning of how the spots should be delivered is performed in a treatment planning system. The treatment planning system determines the energy layers to be used and the distribution and weights of spots therein, but the treatment planning system does not deliver the ion beam. This is done by an ion beam system, to which the treatment planning system is connected in a known way. The size of the spots for a given setup and a given position in the patient is dictated by the ion beam system. There is often a fixed number of spot size settings, but some ion beam systems do allow for control of the spot size in the lateral directions in the same energy layer. The machine setting to obtain a certain spot size for an energy layer may be referred to as a spot size setting.

It is a complex task to determine the distribution of spots in relation to the target volume and the surrounding healthy tissue. The possibility to adjust the spot size, makes this task even more complex.

SUMMARY

It is an object to improve how spots are distributed in and around a target volume, when the size of the spots can be adjusted.

According to a first aspect, it is provided a method for determining a distribution of spots for use with ion beam therapy for providing the spots in a target volume, wherein each spot represents a collection of ions of a specific energy level and of a specific size at a specific lateral location. The method is performed in a treatment planning system and comprises the steps of: dividing the target volume in a plurality of target sections based on a user configuration comprising at least one spot size strategy defining a maximum spot size at the location of a Bragg peak; assigning a spot size strategy to each one of the target sections based on the location of the respective target section; and determining, within each target section, spots in accordance with its spot size strategy.

The step of determining spots comprises determining the spot size for each prospective spot based on tissue that a respective beam path for the spot would pass through the patient.

The step of dividing the target volume in a plurality of target sections may comprise defining an inner target section inside an inner margin, and defining an outer target section between an edge of the target volume and the inner margin, wherein the inner margin is a user configuration parameter defining a margin in relation to the edge of the target volume.

The step of dividing the target volume in a plurality of target sections may comprise defining a plurality of target sections within the target volume delimited from each other by respective inner margins, wherein the inner margins are user configuration parameters defining a respective margin in relation to an edge of the target volume.

The step of dividing the target volume may comprise defining a risk target section between an edge of the target volume and a risk margin, wherein the risk margin is a user configuration defining a margin in relation to an organ at risk.

The spot size strategy for the risk target section may be to use a smallest available spot size.

The step of dividing the target volume may comprise dividing the target volume in target sections according to target section geometries defined in the user configuration.

The user configuration may comprise at least one spot size strategy defining a specific spot size.

All spots may be set to the smallest available spot size setting, even when the maximum spot size at the location of the Bragg peak is exceeded for at least some of the spots.

The user configuration may comprise at least one spot size strategy defining a minimum spot size at the location of a Bragg peak.

All spots may be set to the largest available spot size setting, even when the minimum spot size at the location of the Bragg peak is not reached for at least some of the spots.

According to a second aspect, it is provided a treatment planning system for determining a distribution of spots for use with ion beam therapy for providing the spots in a target volume, wherein each spot represents a collection of ions of a specific energy level and of a specific spot size at a specific lateral location. The treatment planning system comprising: a processor; and a memory storing instructions that, when executed by the processor, cause the treatment planning system to: divide the target volume in a plurality of target sections based on a user configuration comprising at least one spot size strategy defining a maximum spot size at the location of a Bragg peak; assign a spot size strategy to each one of the target sections based on the location of the respective target section; and determine, within each target section, spots in accordance with its spot size strategy.

According to a third aspect, it is provided a treatment planning system for determining a distribution of spots for use with ion beam therapy for providing the spots in a target volume, wherein each spot represents a collection of ions of a specific energy level and of a specific spot size at a specific lateral location. The treatment planning system comprises: means for dividing the target volume in a plurality of target sections based on a user configuration comprising at least one spot size strategy defining a maximum spot size at the location of a Bragg peak; means for assigning a spot size strategy to each one of the target sections based on the location of the respective target section; and means for determining, within each target section, spots in accordance with its spot size strategy.

According to a fourth aspect, it is provided a computer program for determining a distribution of spots for use with ion beam therapy for providing the spots in a target volume, wherein each spot represents a collection of ions of a specific energy level and of a specific spot size at a specific lateral location. The computer program comprises computer program code which, when run on a treatment planning system causes the treatment planning system to: divide the target volume in a plurality of target sections based on a user configuration comprising at least one spot size strategy defining a maximum spot size at the location of a Bragg peak; assign a spot size strategy to each one of the target sections based on the location of the respective target section; and determine, within each target section, spots in accordance with its spot size strategy.

According to a fifth aspect, it is provided a computer program product comprising a computer program according to the fourth aspect and a computer readable means on which the computer program is stored.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

The invention is now described, by way of example, with reference to the accompanying drawings, in which.

DETAILED DESCRIPTION

The invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout the description.

According to embodiments presented herein, a distribution of spots of different sizes is determined for ion beam therapy treatment planning. This is performed by determining target sections, of a target volume, based on user configuration. Each target section is then assigned a spot size strategy. The user configuration is a convenient way to control how spots of different sizes are distributed in the target volume.

Figure 1:
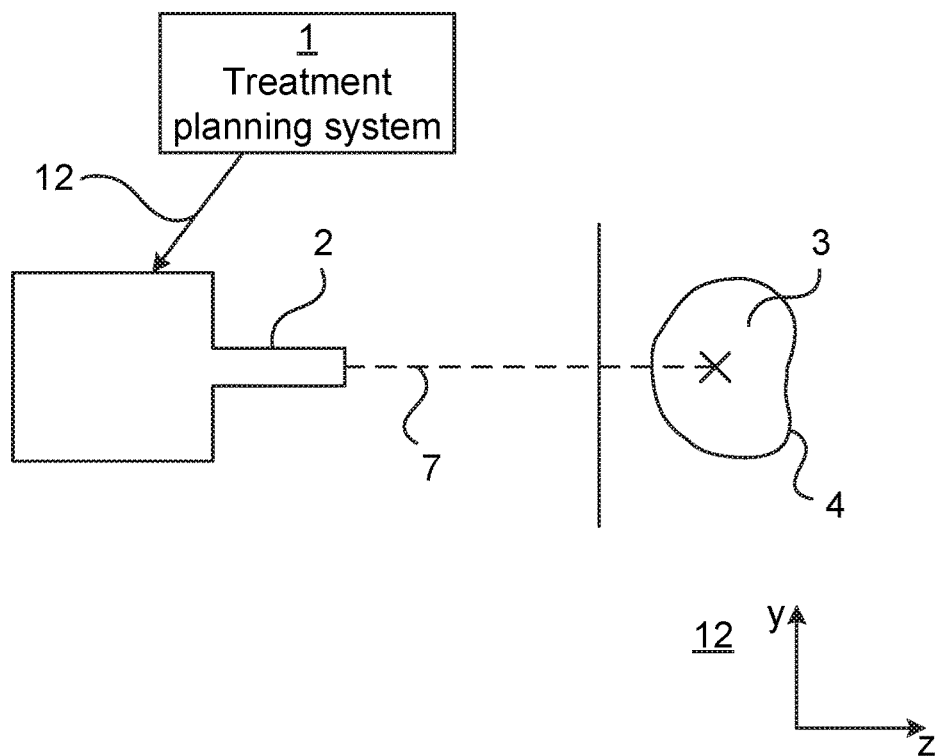
FIG. 1 is a schematic drawing illustrating an environment in which embodiments presented herein can be applied.

FIG. 1 is a schematic drawing illustrating an environment in which embodiments presented herein can be applied. A treatment planning system 1 determines a distribution of spots for ion beam therapy. This is communicated as a spot distribution data set 12 to an ion beam system 2. Based on the spot distribution data set, the ion beam system 2 generates an ion beam 7 for providing spots to a target volume 3 of a patient. The target volume 3 is delimited by an edge 4.

In a coordinate system, the depth is represented along a z-axis and the y-axis is upwards in FIG. 1. The view in FIG. 1 can thus be considered to be a side view. The location of the dose maximum of the spot depth-wise, i.e. along the z-axis, is controlled by the amount of energy provided to the ions; more energy results in a deeper location of the spot dose maximum. Moreover, the lateral position, along the y-axis and x-axis (not shown in FIG. 1), is controlled using electromagnets to deflect the beam 7. In this way, spots can be provided to achieve a dose distribution covering the target volume 3 in three dimensions.

Figure 2:
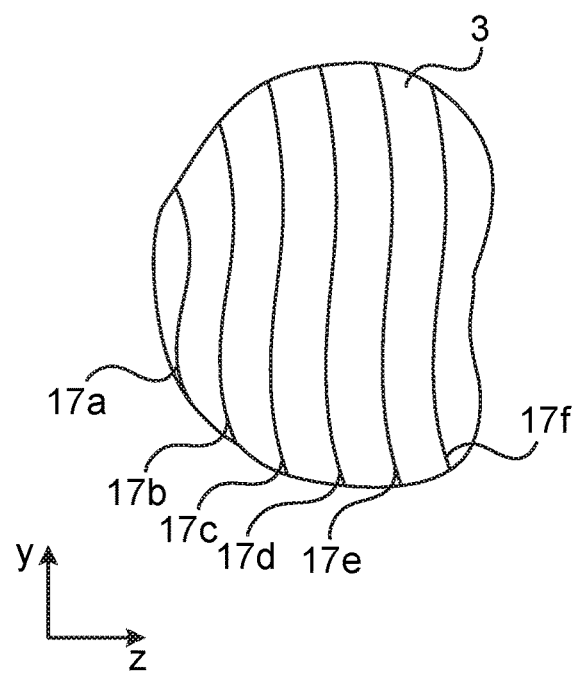
FIG. 2 is a schematic drawing illustrating Bragg peak depths of energy layers in the target volume of FIG. 1.

FIG. 2 is a schematic drawing illustrating energy layers of the target volume 3 of FIG. 1. FIG. 2 is a side view, from the same perspective as the view of FIG. 1. As explained above, the depth (z-direction) of the Bragg peak depends on energy level. Here, there are six energy levels shown as 17a-f in the target volume 3. The energy levels indicate where the Bragg peaks occur for ions at different lateral locations but of the same energy. For instance, a first energy level 17a shows where the Bragg peaks occur when ions of a first amount of energy are supplied using the ion beam therapy in the system of FIG. 1. A second energy level 17b shows where the Bragg peaks occur when ions of a second amount of energy are supplied, etc. It is to be noted that the density of tissue that the ion beam passes through affects the depth (and spot size). For instance, if the beam passes through bone this results in a different depth of the Bragg peak than if the beam passes through muscle tissue. Consequently, each energy level 17a-f does not need to be a straight line of a certain depth.

Figure 3:
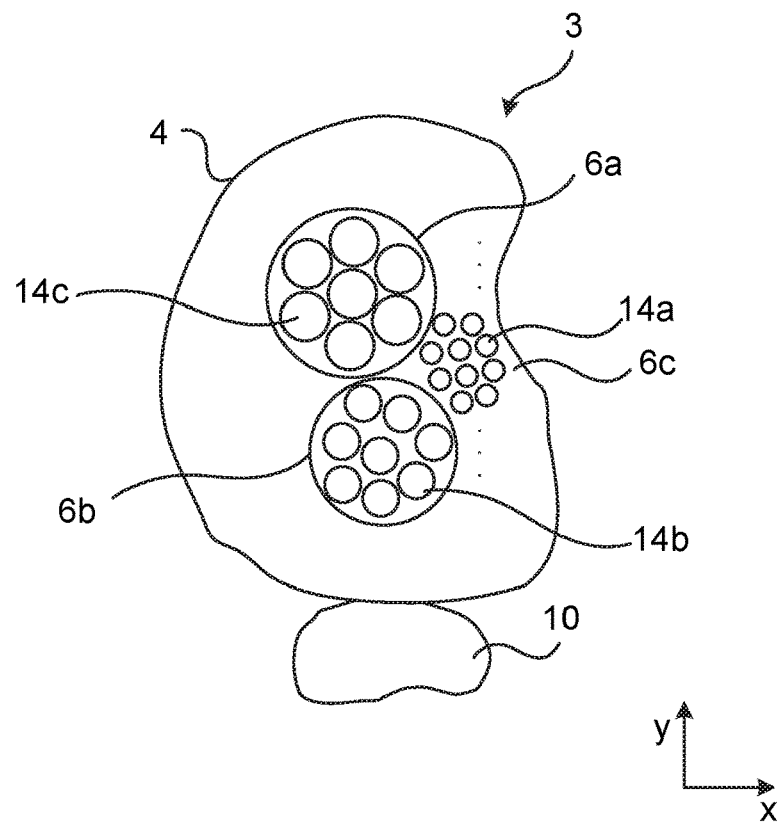
FIG. 3 is a schematic drawing illustrating an embodiment where spot sizes are determined based on target section geometries defined in a user configuration.

FIG. 3 is a schematic drawing illustrating an embodiment where spot sizes are determined based on target section geometries defined in a user configuration. An energy layer (one of the energy layers 17a-f of FIG. 2) is shown along an x-y plane. While the energy layer does not need to be completely flat in the target volume of the patient, the energy layer is here depicted as a flattened layer, as it would look if the patient were not present. The treatment planning system 1 can calculate the z position of the Bragg peak of any spot of each energy layer, and can thus transform any spot location on the energy layer, in a flattened two dimensional space, and a location of the Bragg peak in a three dimensional space, taking the tissue in the patient into account.

The target volume 3 is here divided in target sections 6a-c according to target section geometries defined in a user configuration. For instance, the user configuration can define a first geometry as a volume within the target volume 3, whereby the first geometry defines a first target section 6a. A second geometry is a separate (non-overlapping) volume within the target volume, whereby the second geometry defines a second target section 6b. Optionally, if the first and second geometries intersect, the user configuration can define which one of the first target section and the second target section that the intersecting volume should belong to.

A third geometry can then be defined as the part of the target volume 3 that is neither part of the first geometry nor the second geometry. The third geometry defines the third target section 6c.

Each one of the target sections 6a-c can be assigned its own spot size strategy. The spot size strategies are defined in more detail below. In one embodiment, each spot size strategy implies a certain fixed spot size. In this example, the third target section 6c is assigned a spot size strategy defining small spots 14a, being spots of a specified (in this context small) size. The second target section 6b is assigned a spot size strategy defining medium sized spots 14b, being spots of a specified (in this context medium) size. The first target section 6a is assigned a spot size strategy defining large spots 14c, being spots of a specified (in this context large) size. It is to be noted that the spot sizes could vary both within a continuous range and in discrete steps.

It is to be noted that, while not explicitly shown in FIG. 3, the small spots 14a fill the entire second target section 6c.

While FIG. 3 only discloses the spot distribution of one energy layer, there are corresponding spot distributions determined for each energy layer to be used for a target volume. These spot distributions can be based on the same criteria (target sections and spot size strategies) as for the energy layer shown in FIG. 3. The target sections are defined in three dimensions, but are transferred to two-dimensional sections in each energy layer to allow the placement of spots in each energy layer according to the corresponding spot size strategy. It is to be noted that, for a particular spot size setting, the actual spot size depends on the energy layer.

Figure 4A:
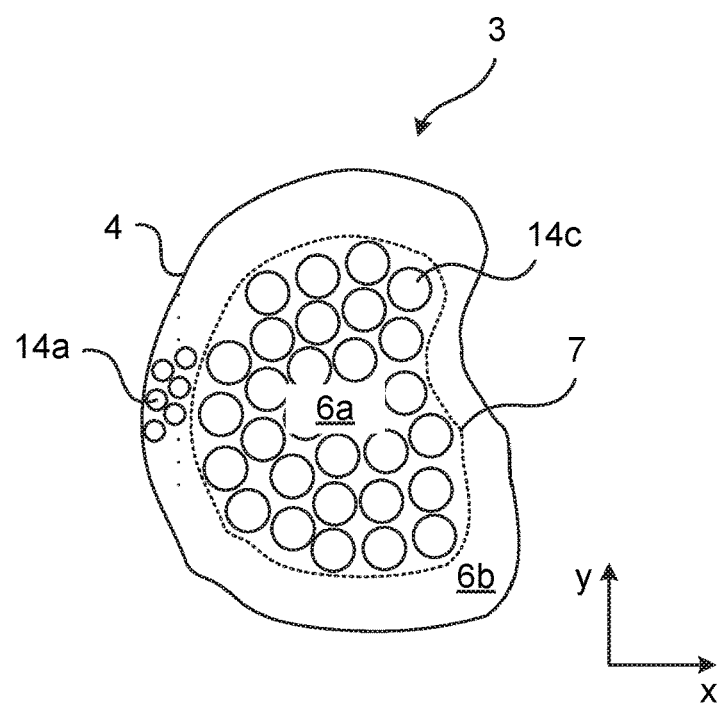
FIGS. 4A-C are schematic drawing illustrating an embodiment where spot sizes are determined based on user configuration comprising one or more margins.
Figure 4B:
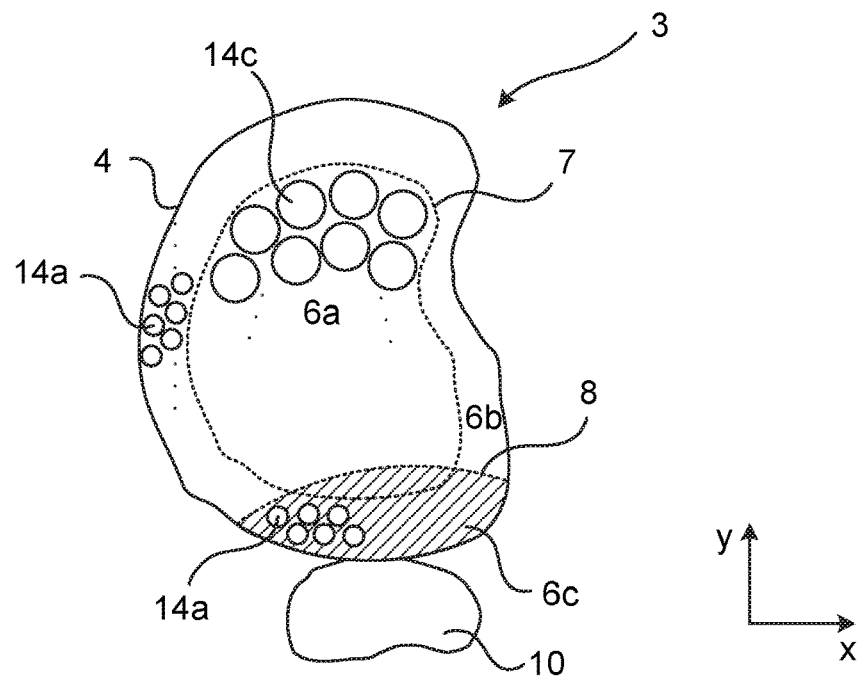
Figure 4C:
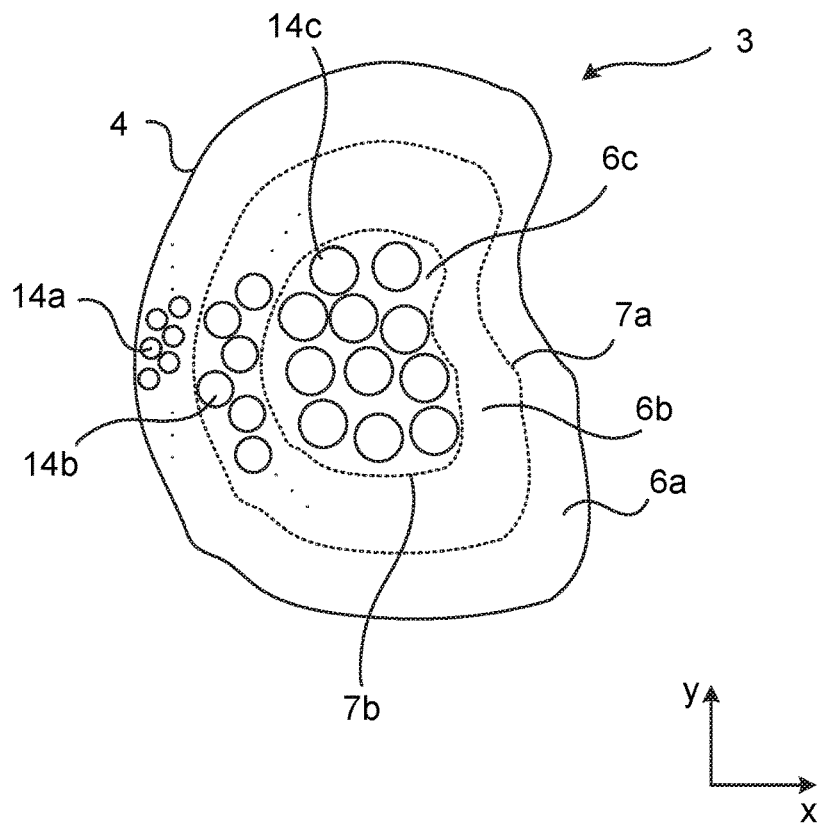

FIGS. 4A-C are schematic drawing illustrating an embodiment where spot sizes are determined based on user configuration comprising one or more margins. As for FIG. 3, the spots are shown in a single energy layer.

Looking first at FIG. 4A, there is one margin, an inner margin 7 from the edge 4 of the target volume 3. The term 'inner' is here to be interpreted in relation to the edge 4 of the target volume 3. The inner margin 7 is a user configuration parameter defining a margin in relation to the edge 4 of the target volume 3. The inner margin defines an inner target section 6a inside the inner margin 7, and an outer target section 6b between an edge 4 of the target volume 3 and the inner margin 7.

As for the embodiment illustrated in FIG. 3, each target section can be assigned its own spot size strategy. For instance, the inner target section 6a can be assigned a spot size strategy defining large spots 14c while the outer target section 6b can be assigned a spot size strategy defining small spots 14a.

Smaller spots result in a smaller beam penumbra (i.e. a steeper dose fall-off outside the edge of the target volume), whereby it is beneficial to have smaller spots close to the edge 4 of the target volume 3, i.e. in the second target section 6b to prevent providing unnecessary dose to tissue surrounding the target volume. Moreover, in order to reduce treatment time and improve robustness, it is beneficial to have larger spots in the centre of the target volume, i.e. in the first target section 6a, where the larger spots have lower effect on the penumbra. Robust is here to be interpreted as robust with respect to patient setup and density estimation errors, as well as errors arising due to organ motion including any interference with the delivery, i.e. that the dose distribution is suitable even if any of these errors occur.

Using the single user configuration parameter of the inner margin, such the spot size population is achieved very conveniently. It is to be noted that, while not explicitly shown in FIG. 4A, the small spots 14a fill the entire second target section 6b.

Looking now to FIG. 4B, in addition to the embodiment illustrated by FIG. 4A, there is here a risk margin 8 defining a risk target section 6c between the edge 4 of the target volume 3 and the risk margin 8. The risk margin 8 is a user configuration defining a margin in relation to an organ at risk 10. The provision of any dose should be minimised to the organ at risk 10. The risk target section 6c can be assigned its own spot size strategy. For instance, the risk target section 6c can be assigned a spot size strategy defining the small spots 14a to minimise the dose that falls within the organ at risk 10.

It is to be noted that, while not explicitly shown in FIG. 4B, the small spots 14a fill the entire second target section 6b and the entire third target section 6c, and the large spots 14c fill the entire first target section 6a.

Looking now to FIG. 4C, a plurality of target sections 6a-6c are defined within the target volume 3 which are delimited from each other by respective inner margins 7a-b. The inner margins 7a-b are user configuration parameters defining a respective margin in relation to the edge 4 of the target volume 3. In this example, there is a first inner margin 7a and a second inner margin 7b, wherein the second inner margin 7b is inside the first inner margin 7a. A first target section 6a is thus defined between the edge 4 of the target volume 3 and the first inner margin 7a. A second target section 6b is defined between the first inner margin 7a and the second inner margin 7b. A third target section 6c is defined inside the second inner margin 7b.

It is to be noted that, while not explicitly shown in FIG. 4C, the small spots 14a fill the entire third target section 6c and the medium spots 14b fill the entire second target section 6b.

While FIGS. 4A-C only disclose the spot distribution of one energy layer, there are corresponding spot distributions determined for each energy layer to be used for a target volume, which spot distributions can be based on the same criteria (margin(s)) as for the energy layer shown in FIGS. 4A-C. It is to be noted that, for a particular spot size setting, the actual spot size at the Bragg peak depends on the energy of the ions and the tissue the ions have traversed.

Figure 5:
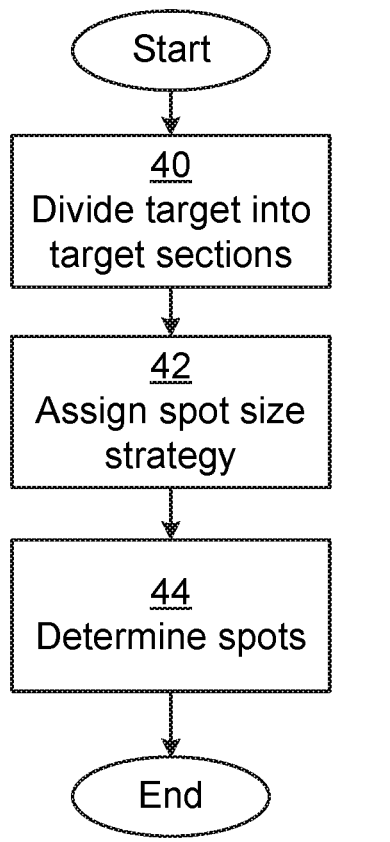
FIG. 5 is a flow chart illustrating embodiments of a method for determining a distribution of spots, the method being performed in the treatment planning system of FIG. 1.

FIG. 5 is a flow chart illustrating embodiments of a method for determining a distribution of spots. The method is performed in the treatment planning system (see 1 of FIG. 1). As described above, the distribution of spots is intended to be used with ion beam therapy for providing the spots in a target volume. Each spot represents a collection of ions of a specific energy level and of a specific spot size at a specific lateral location.

In a divide target into target sections step 40, the treatment planning system divides the target volume in a plurality of target sections based on a user configuration comprising at least one spot size strategy defining a maximum spot size at the location of a Bragg peak. The maximum spot size can vary for different regions.

In one embodiment, this comprises defining an inner target section inside an inner margin (see 6a of FIG. 4A), and defining an outer target section between an edge of the target volume and the inner margin (see e.g. 6b of FIG. 4A). The inner margin (see 7 of FIG. 4A) is a user configuration parameter defining a margin in relation to the edge (see 4 of FIG. 4A) of the target volume.

In one embodiment, a plurality of target sections are defined within the target volume. The target sections are delimited from each other by respective inner margins (see 7a-b of FIG. 4C), wherein the inner margins are user configuration parameters defining a respective margin in relation to the edge of the target volume. In other words, there are here several margins defining sections successively closer to the centre of the target volume, e.g. as shown in FIG. 4C and described above. This gives a possibility of providing a greater granularity in how the spot sizes are applied for the target volume, compared to using only one inner margin.

Optionally, a risk target section (see 6c of FIG. 4B) between an edge of the target volume and a risk margin (see 8 of FIG. 4B) is defined. The risk margin is a user configuration defining a margin in relation to an organ at risk. In this way, a particularly careful spot size strategy can be applied for the target volume close to the organ at risk, to minimise any risk of beam dose being delivered to the organ at risk.

In one embodiment, the target volume is divided into target sections according to target section geometries defined in the user configuration, e.g. as shown in FIG. 3 and described above. This allows a completely flexible way for the user to define the target volumes.

In an assign spot size strategy step 42, a spot size strategy is assigned to each one of the target sections based on the location of the respective target section.

In one embodiment, the spot size strategy for the risk target section is to use a smallest available spot size setting. This may be useful to minimise any risk of delivering beam dose to the organ at risk.

Optionally, the user configuration comprises at least one spot size strategy defining a specific spot size. For instance, the small, medium and large spot sizes of FIGS. 3 and FIGS. 4A-C are examples of such spot size strategy.

The maximum spot size can be the same for all energy layers or could differ between energy layers. A maximum spot size can be useful to achieve a sharper dose fall-off around the target edges. As have been described above, a specific spot size setting will result in an actual spot size at the location of the Bragg peak which is dependent on the energy level and the traversed tissue. For instance, when the beam traverses bone matter, the beam spreads, leading to a larger spot size. Hence, the spot size is determined based on the tissue that a respective beam path for the spot would pass through the patient. When a maximum spot size is defined, the spot size setting in the specific energy layer shall be chosen such that all spots have actual sizes at the location of the Bragg peak which are smaller or equal to the maximum actual spot size.

However, there can exist spots, for which the actual spot size of the smallest available spot size setting at the location of the Bragg peak is greater than the maximum spot size of its spot size strategy. Such spots can then not be smaller than what is possible for the energy level, and are thus set to the smallest available spot size setting, even when the maximum spot size at the location of the Bragg peak is exceeded for at least some of the spots, i.e. when this results in an actual spot size which is larger than the maximum spot size.

Optionally, the user configuration comprises at least one spot size strategy defining a minimum spot size at the location of the Bragg peak, i.e. for one or more particular energy layers. The minimum spot size can be the same for all energy layers or could differ between energy layers. The maximum spot size can also vary for different regions within an energy layer. A minimum spot size can be useful to provide a certain robustness and/or to prevent treatment time from being too long. When a minimum spot size is defined, the spot size setting in the specific energy layer shall be chosen such that all spots have actual sizes at the location of the Bragg peak which are larger or equal to the minimum actual spot size.

However, there can exist spots, for which the actual spot size of the largest available spot size setting at the location of the Bragg peak is smaller than the minimum spot size of its spot size strategy. Such spots can then not be larger than what is possible for the energy level, and are thus set to the largest available spot size setting, even when the minimum spot size at the location of the Bragg peak is not reached for at least some of the spots, i.e. this results in an actual spot size which is smaller than the minimum spot size.

It is to be noted that the spot sizes could vary both within a continuous range and in discrete steps.

In a determine spots step 44, the treatment planning system determines, within each target section, spots in accordance with its spot size strategy.

The spot size for each prospective spot can be determined based on tissue that a respective beam path for the spot would pass through the patient. In other words, the spot size is determined based on three dimensional data defining the type of tissue of the patient that each beam would pass through. For instance, a beam passing through bone tissue spreads more and leads to a larger spot size than a beam of the same energy which does not pass through bone tissue.

This method could be applied in both continuous scanning (line scanning) and in discrete spot scanning (step-and-shoot spot scanning).

The method provided allows a selection of spot sizes to achieve several beneficial effects. Small spot sizes will give smaller lateral penumbrae. However, many small spots will prolong the treatment time. Hence, larger spots can be used in the central area of the target volume, since spots in this area will affect the beam penumbra to a smaller extent. The larger spots result in shorter treatment time and improved robustness.

Figure 6:
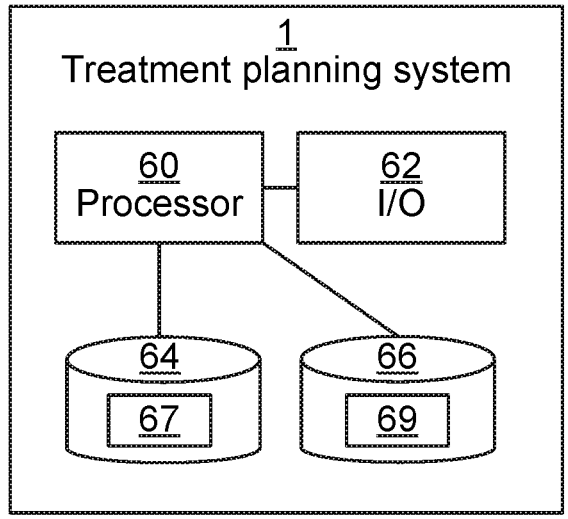
FIG. 6 is a schematic diagram illustrating components of the treatment planning system of FIG. 1 according to one embodiment.

FIG. 6 is a schematic diagram illustrating components of the treatment planning system 1 of FIG. 1 according to one embodiment. A processor 60 is provided using any combination of one or more of a suitable central processing unit (CPU), multiprocessor, microcontroller, digital signal processor (DSP), application specific integrated circuit etc., capable of executing software instructions 67 stored in a memory 64, which can thus be a computer program product. The processor 60 can be configured to execute the method described with reference to FIG. 5 above.

The memory 64 can be any combination of random access memory (RAM) and read only memory (ROM). The memory 64 also comprises persistent storage, which, for example, can be any single one or combination of magnetic memory, optical memory, solid-state memory or even remotely mounted memory.

A data memory 66 is also provided for reading and/or storing data during execution of software instructions in the processor 60. The data memory 66 can be any combination of random access memory (RAM) and read only memory (ROM). The data memory 66 can e.g. contain a user configuration 69.

The treatment planning system 1 further comprises an I/O interface 62 for communicating with other external entities. Optionally, the I/O interface 62 also includes a user interface.

Other components of the treatment planning system 1 are omitted in order not to obscure the concepts presented herein.

Figure 7:
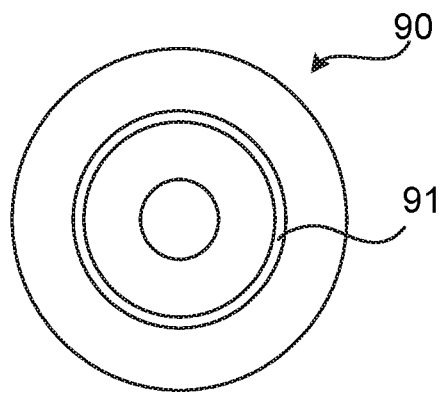
FIG. 7 shows one example of a computer program product comprising computer readable means.

FIG. 7 shows one example of a computer program product 90 comprising computer readable means. On this computer readable means, a computer program 91 can be stored, which computer program can cause a processor to execute a method according to embodiments described herein. In this example, the computer program product is an optical disc, such as a CD (compact disc) or a DVD (digital versatile disc) or a Blu-Ray disc. As explained above, the computer program product could also be embodied in a memory of a device, such as the computer program product 64 of FIG. 6. While the computer program 91 is here schematically shown as a track on the depicted optical disk, the computer program can be stored in any way which is suitable for the computer program product, such as a removable solid state memory, e.g. a Universal Serial Bus (USB) drive.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A method for determining a distribution of spots for use with ion beam therapy for providing the spots in a target volume, wherein each spot represents a collection of ions of a specific energy level and of a specific size at a specific lateral location, the method being performed in a processor of a treatment planning system and comprising the steps of:
dividing, by the processor, the target volume in a plurality of non-overlapping target sections and comprising an outer target section defining a first inner margin, an inner target section defining a second inner margin, and an intermediate target section defined by the first and second inner margins, based on a user configuration comprising a plurality of spot size strategies, each with a different spot size, defining a maximum spot size at a location of a Bragg peak;
assigning, by the processor, a spot size strategy from the plurality of spot size strategies to each one of the target sections based on the location of the respective target section such that the outer target section is assigned a first spot size, the intermediate target section is assigned a second spot size greater than the first spot size, and the inner target section is assigned a third spot size greater than the second spot size;
determining, by the processor within each target section, spots to fill the respective target section in accordance with the respective spot size strategy; and
generating, using the determined spots, a spot distribution data set, which is communicated to an ion beam system configured to generate at least one ion beam to the target volume according to the determined spots during the ion beam therapy.

2. The method according to claim 1, wherein the step of determining spots comprises determining, by the processor, the spot size for each prospective spot based on tissue that a respective beam path for the spot would pass through a patient.

3. The method according to claim 1, wherein the step of dividing the target volume in the plurality of non-overlapping target sections comprises defining the inner target section inside the second inner margin, and defining the outer target section between an edge of the target volume and the first inner margin, wherein each of the first inner margin and the second inner margin is a user configuration parameter defining a margin in relation to the edge of the target volume.

4. The method according to claim 1, wherein the step of dividing the target volume in the plurality of non-overlapping target sections comprises defining a plurality of target sections within the target volume delimited from each other by the respective first and second inner margins, wherein the first and second inner margins are user configuration parameters defining a respective margin in relation to an edge of the target volume.

5. The method according to claim 1, wherein the step of dividing the target volume comprises defining a risk target section between an edge of the target volume and a risk margin, wherein the risk margin is a user configuration defining a margin in relation to an organ at risk.

6. The method according to claim 5, wherein the spot size strategy for the risk target section is to use a smallest available spot size.

7. The method according to claim 1, wherein the step of dividing the target volume comprises dividing the target volume in target sections according to target section geometries defined in the user configuration.

8. The method according to claim 1, wherein all spots are set to a smallest available spot size setting resulting in an actual spot size for at least some of the spots to be larger than the maximum spot size.

9. The method according to claim 1, wherein the user configuration comprises at least one spot size strategy defining a minimum spot size at the location of a Bragg peak.

10. The method according to claim 9, wherein all spots are set to a largest available spot size setting resulting in an actual spot size for at least some of the spots to be smaller than the minimum spot size.

11. A non-transitory computer-readable medium storing therein a computer program which, when executed on the processor of the treatment planning system, performs the method according to claim 1.

12. A treatment planning system for determining a distribution of spots for use with ion beam therapy for providing the spots in a target volume, wherein each spot represents a collection of ions of a specific energy level and of a specific spot size at a specific lateral location, the treatment planning system comprising:
a processor; and a memory storing instructions that, when executed by the processor, cause the processor of the treatment planning system to:

divide the target volume in a plurality of non-overlapping target sections and comprising an outer target section defining a first inner margin, an inner target section defining a second inner margin, and an intermediate target section defined by the first and second inner margins, based on a user configuration;

assign a different spot size strategy to each one of the target sections based on the location of the respective target section, wherein each spot size strategy has a different spot size such that the outer target section is assigned a first spot size, the intermediate target section is assigned a second spot size greater than the first spot size, and the inner target section is assigned a third spot size greater than the second spot size;

determine, within each target section, spots to fill the respective target section in accordance with the respective spot size strategy; and generate, using the determined spots, a spot distribution data set which is communicated to an ion beam system configured to generate at least one ion beam to the target volume according to the determined spots during the ion beam therapy.

13. A treatment planning system for determining a distribution of spots for use with ion beam therapy for providing the spots in a target volume, wherein each spot represents a collection of ions of a specific energy level and of a specific spot size at a specific lateral location, the treatment planning system comprising:

a processing means for dividing the target volume in a plurality of non-overlapping target sections comprising an outer target section defining a first inner margin, an inner target section defining a second inner margin, and an intermediate target section defined by the first and second inner margins, based on a user configuration comprising a plurality of spot size strategies, each with a different spot size, defining a maximum spot size at the location of a Bragg peak;

a processing means for assigning a spot size strategy from the plurality of spot size strategies to each one of the target sections based on the location of the respective target section such that the outer target section is assigned a first spot size, the intermediate target section is assigned a second spot size greater than the first spot size, and the inner target section is assigned a third spot size greater than the second spot size; and a processing means for determining, within each target section, spots to fill the respective target section in accordance with the respective spot size strategy and generating, using the determined spots, a spot distribution data set which is communicated to an ion beam system configured to generate at least one ion beam to the target volume according to the determined spots during the ion beam therapy.

\* \* \* \* \*